US007268262B2

United States Patent
Graybill et al.

(10) Patent No.: US 7,268,262 B2
(45) Date of Patent: Sep. 11, 2007

(54) METHOD FOR RECOVERING TRANS-1,2-DICHLOROETHENE

(75) Inventors: Clark S. Graybill, Lake Charles, LA (US); Stephen R. Lester, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 479 days.

(21) Appl. No.: 10/834,408

(22) Filed: Apr. 29, 2004

(65) Prior Publication Data

US 2005/0245775 A1 Nov. 3, 2005

(51) Int. Cl.
*C07C 17/358* (2006.01)
*C07C 21/02* (2006.01)
(52) U.S. Cl. .............. 570/236; 570/202; 570/216; 570/235; 570/256
(58) Field of Classification Search .......... 570/236, 570/202, 216, 235, 256
See application file for complete search history.

(56) References Cited

U.S. PATENT DOCUMENTS 3,914,167 A  10/1975  Ivy et al. ............... 204/163 R
4,781,807 A  11/1988  Clark, Jr. et al. ....... 204/157.98
5,051,536 A   9/1991  Gorton et al. .............. 570/236

FOREIGN PATENT DOCUMENTS

WO    WO91/02708    3/1991

*Primary Examiner*—Thurman K. Page
*Assistant Examiner*—Yevgeny Valenrod
(74) *Attorney, Agent, or Firm*—Linda Pingitore

(57) ABSTRACT

Describes a method for recovering trans-1,2-dichloroethene from a liquid feed composition comprising both the cis-and trans-isomers of 1,2-dichloroethene and contaminating amounts of other chlorinated hydrocarbons, e.g., lower alkyl chlorinated hydrocarbons, such as $C_1\text{-}C_2$ chlorinated hydrocarbons. In one of the described methods, the liquid feed composition is introduced into a first distillation column 10 wherein the stereoisomers and chlorinated hydrocarbons more volatile than the stereoisomers are removed as overhead 12 and charged to a second distillation column 20. In column 20, the stereoisomers are separated from the more volatile chlorinated hydrocarbons, and a bottoms fraction 24 comprising the stereoisomers is charged to a reactive distillation column 30 wherein the cis-isomer is isomerized to the trans-isomer in the liquid phase and in the presence of an organic free-radical initiator, e.g., an azonitrile initiator. Substantially pure trans 1,2-dichloroethene is recovered as overhead 32 from reactive distillation column 30.

41 Claims, 1 Drawing Sheet

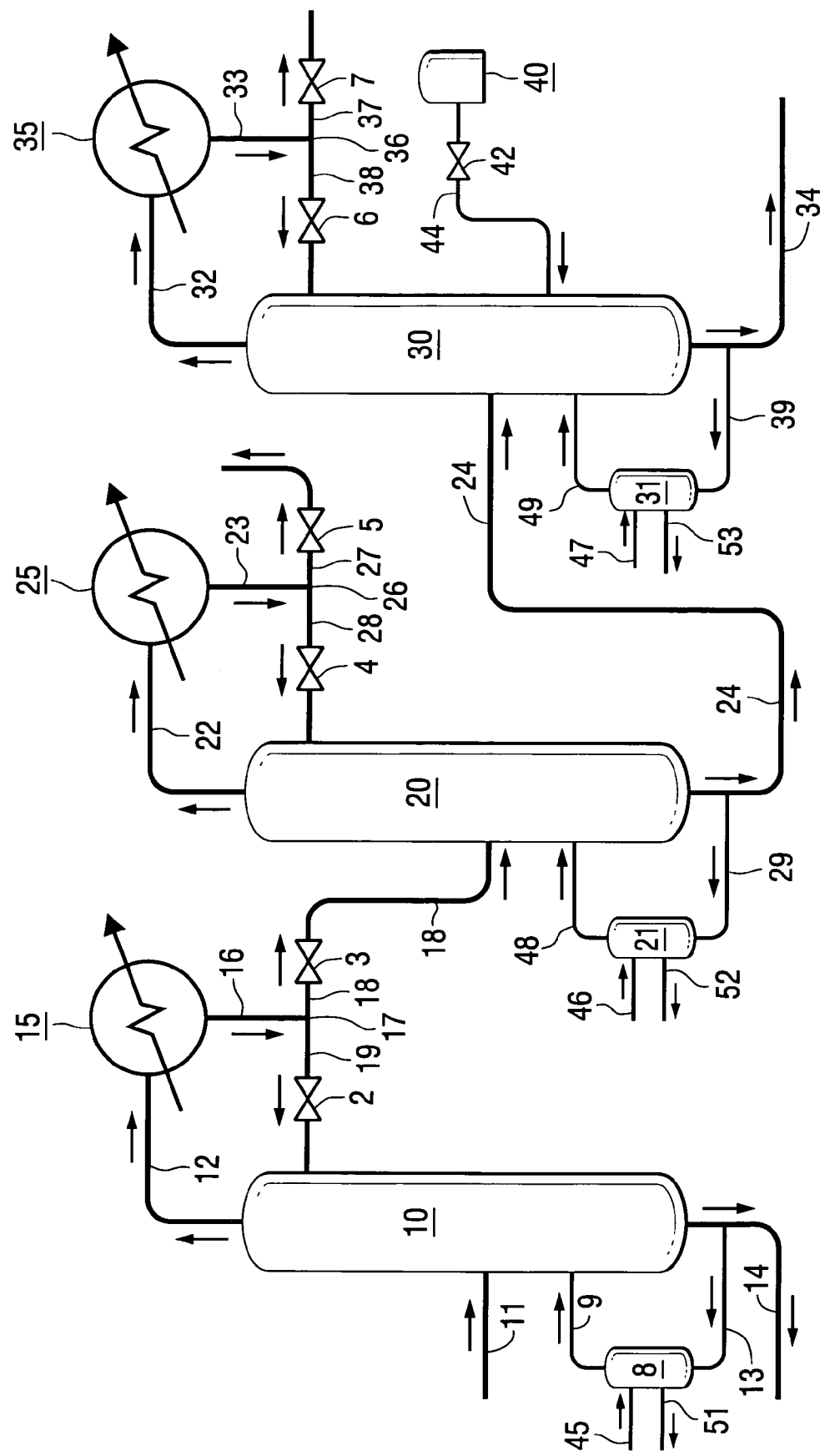

METHOD FOR RECOVERING TRANS-1,2-DICHLOROETHENE

BACKGROUND OF THE INVENTION 1,2-Dichloroethene [CAS 540-59-0] exists as a mixture of two isomers; namely, the trans isomer [CAS 156-60-5] and the cis isomer [CAS 156-59-2]. Both isomers are valuable compounds having a variety of uses. The isomers can be used separately or together in various proportions. It is reported that 1,2-dichloroethene can be used as a low temperature extraction solvent for organic materials, such as dyes, perfumes, lacquers and thermoplastics, as a solvent for the manufacture of rubber solutions, as a coolant in refrigeration plants, and as a chemical intermediate in the synthesis of other chlorinated hydrocarbon solvents.

1,2-Dichloroethene can be produced by the direct chlorination of acetylene at from approximately 40° C. to 80° C., by the reduction of 1,1,2,2-tetrachloroethane, by the pyrolytic dehydrochlorination of 1,1,2-trichloroethane, or as a by-product in the production of other $C_2$ chlorinated hydrocarbons, e.g., trichloroethylene. However produced, the 1,2-dichloroethene product comprises a mixture of the trans and cis isomers, the quantity of which 1,2-dichloroethene product depending upon the conditions and process of manufacture, particularly when the 1,2-dichloroethene is recovered as a by-product. Mixtures of the trans and cis isomers of 1,2-dichloroethene typically exist as an equilibrium mixture, with the equilibrium concentration ratio of cis:trans being reported as being from approximately 2:1 to 5:1, depending upon the temperature and pressure of the mixture. At 825° C., for example, the equilibrium mixture contains about 55 percent of the cis-isomer; while at 975° C., the proportion of the cis-isomer falls to 52 percent. See, U.S. Pat. No. 5,051,536.

For some uses, trans-1,2-dichloroethene or a trans-rich mixture of the two stereoisomers is favored. Trans-1,2-dichloroethene is more reactive chemically than the cis-isomer, especially in 1,2-addition reactions. It also has a lower normal boiling point and a lower latent heat of vaporization than the cis-isomer. Consequently, the trans isomer or a trans-rich mixture is favored for extractions where it is desired to recover the 1,2-dichloroethene by distillation for recycle. The trans-isomer also has a lower viscosity than the cis-isomer, so that less energy is required for pumping the trans-isomer or trans-rich mixture.

For other uses, cis-1,2-dichloroethene or a cis-rich mixture of the two stereoisomers is favored. Since the cis-isomer has a lower melting point than the trans-isomer, the cis-isomer or a cis-rich mixture is better suited for use as an indirect heat transfer medium in refrigeration systems operating at low temperatures. The solubility of the cis-isomer in water at 25° C. is less than that of the trans-isomer, so that the cis-isomer or a cis-rich mixture of the stereoisomers is favored for some extractions where an aqueous phase is present. The lower chemical reactivity of the cis-isomer or a cis-rich mixture is also better suited where chemical stability is desired.

When the trans-isomer or a trans-rich mixture is required, it is desirable to be able to isomerize the cis-isomer to the trans-isomer. U.S. Pat. No. 5,051,536 describes isomerization of 1,2-dichloroethene isomers in the liquid phase in the presence of a free-radical initiator. In the embodiment described in Example 1 of the '536 patent, a feed comprising a mixture of 1,2-dichloroethene (cis and trans isomers) and other $C_1$ and $C_2$ chlorinated hydrocarbons is used to illustrate the conversion of the cis-isomer to the trans-isomer in the liquid phase at reflux conditions and in the presence of a free-radical initiator. When the trans-1,2-dichloroethene product is recovered as an overhead stream from this conversion reaction, the '536 patent suggests that it can be further purified by a subsequent distillation to yield a trans product with an assay of greater than 95 weight percent.

It has been observed that the overall recovery of trans-1,2-dichloroethene for the method described in the '536 patent is on the order of 45 to 60 percent, based on the amount of 1,2-dichloroethene isomers in the feed composition. It would, therefore, be desirable to increase the overall recovery of the trans-1,2-dichloroethene isomer from such a process.

DESCRIPTION OF THE INVENTION

In accordance with the present invention, there is described a method for recovering trans-1,2-dichloroethene with significantly improved efficiencies from a liquid feed composition comprising the cis and trans stereoisomers of 1,2-dichloroethene and contaminating amounts, e.g., substantial contaminating amounts, of other chlorinated hydrocarbons.

For purposes of this specification (other than in the operating examples), unless otherwise indicated, all numbers expressing quantities and ranges of ingredients, reaction conditions, etc., are to be understood as modified in all instances by the term "about". Accordingly, unless indicated to the contrary, the numerical parameters set forth in this specification and attached claims are approximations that can vary depending upon the results sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Further, as used in this specification and the appended claims, the singular forms "a", "an" and "the" are intended to include plural referents, unless expressly and unequivocally limited to one referent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Also, it should be understood that any numerical range recited herein is intended to include all sub-ranges subsumed therein. For example, a range of "1 to 10" is intended to include all sub-ranges between and including the recited minimum value of 1 and the recited maximum value of 10, e.g., a range having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

In accordance with the improved method described herein, the feed is distilled in a first distillation zone and a composition comprising the cis- and trans-isomers of 1,2-dichloroethene is recovered either as (1) an overhead stream comprising the stereoisomers and chlorinated hydrocarbons having a lower boiling temperature than said stereoisomers, or (2) a stream comprising said stereoisomers and chlorinated hydrocarbons having a higher boiling temperature than said stereoisomers. At least a portion of the composition comprising the stereoisomers is distilled in a second distillation zone. A composition comprising principally the stereoisomers is recovered from the second distillation zone, and at least a portion of this composition is introduced into a reactive distillation zone containing organic free-radical initiator. Cis-1,2-dichloroethene is isomerized into trans-1,2-dichloroethene in the reactive distillation zone, and a product comprising substantially pure trans-1,2-dichloroethene is recovered from said reactive distillation zone.

In one embodiment of the improved method, the feed composition comprising the stereoisomers and contaminating amounts of other chlorinated hydrocarbons are distilled in a first distillation zone to initially separate the 1,2-dichloroethene isomers and chlorinated hydrocarbons more volatile than the 1,2-dichloroethene isomers from the feed containing these materials and other less volatile chlorinated hydrocarbons. Subsequently, the chlorinated hydrocarbons more volatile than the 1,2-dichloroethene isomers are separated from the 1,2-dichloroethene isomer mixture recovered from the first distillation zone before isomerizing the cis-isomer present in the 1,2-dichloroethene isomer mixture to the trans-isomer in a reactive distillation zone. By this technique, the overall recovery of the trans-1,2-dichloroethene isomer can be substantially increased, e.g., to at least 90 percent, and the trans-1,2-dichloroethene isomer is recovered as a substantially pure product that does not typically require any further purification, e.g., by distillation.

In a further embodiment of the present method, the distillate from the first distillation zone comprises chlorinated hydrocarbons more volatile than the stereoisomers (a light fraction), while a composition comprising the stereoisomers and chlorinated hydrocarbons less volatile than the stereoisomers (a heavy fraction) are recovered from the first distillation column. Subsequently, at least a portion of this heavy fraction is distilled in a second distillation zone from which is recovered as an overhead fraction a stream comprising principally trans-1,2-dichloroethene and cis-1,2-dichloroethene. At least a portion of this overhead fraction from the second distillation zone is introduced into a reactive distillation zone wherein cis-1,2-dichloroethene is isomerized to trans-1,2-dichloroethene in the liquid phase and in the presence of free-radical initiator.

BRIEF DESCRIPTION OF THE DRAWING

The FIGURE of this application is a schematic of a flow diagram of one embodiment of the present invention illustrating three distillation columns in series.

DETAILED DESCRIPTION OF THE INVENTION

The method of the present invention is directed to recovering trans-1,2-dichloroethene in high yields from a liquid composition comprising both the cis and trans isomers of 1,2-dichloroethene and substantial contaminating amounts of other chlorinated hydrocarbons, e.g., $C_1$ and/or $C_2$ chlorinated hydrocarbons. By substantial contaminating amounts means that the liquid composition comprises at least 20 weight percent, often at least 25 weight percent, more often at least 30 weight percent, e.g., from 30 to 35 weight percent of $C_1$ and/or $C_2$ chlorinated hydrocarbons. Also, the liquid composition typically comprises less than 80 weight percent, often less than 75 weight percent, more often less than 70 weight percent, and usually less than 65, e.g., less than 50, weight percent of $C_1$ and/or $C_2$ chlorinated hydrocarbons. The amount of $C_1$ and/or $C_2$ chlorinated hydrocarbons in the liquid composition can vary between any combination of any of the stated lower and any of the stated and higher values, inclusive of the recited values, e.g., between any combination of the stated lower values, or between any combination of the stated higher values.

The amount of the cis- and trans-1,2-dichloroethene isomers in the liquid feed composition is typically the value obtained by subtracting the amount of $C_1$ and/or $C_2$ chlorinated hydrocarbons in the liquid composition from 100 percent, although the amount of cis- and trans-1,2-dichloroethene in the liquid composition can be slightly less than the aforedescribed calculated amount due to the presence of small, e.g., trace, amounts of other non-chlorinated hydrocarbons, e.g., hydrogen chloride and water, in the liquid feed composition. Generally, the amount of cis-1,2-dichloroethene in the liquid composition used in the method of the present invention can vary from approximately 20 to 50 weight percent, e.g., 25 to 45 weight percent; while the amount of trans-1,2-dichloroethene in the liquid composition can vary from approximately 5 to 50 weight percent, e.g., 10 to 40 weight percent. The amounts of the cis- and the trans-isomers in the liquid composition can range between any combination of any of the stated lower and higher values, inclusive of the recited values. The total amount of the cis- and trans-isomers of 1,2-dichloroethene in the liquid feed composition is, of course, the sum of the values for both the cis- and trans-isomers.

As mentioned elsewhere herein, the amount of the cis- and trans-isomers of 1,2-dichloroethene and the quantity and identity of the other chlorinated hydrocarbons, e.g., $C_1$ and/or $C_2$ chlorinated hydrocarbons, in the liquid composition will depend on the process that is used to prepare 1,2-dichloroethene, e.g., the process that is used to prepare chlorinated hydrocarbons from which the liquid composition containing 1,2-dichloroethene isomers that is used in the present method is obtained. For example, 1,2-dichloroethene can be produced as a by-product during the production of trichloroethylene and perchloroethylene by the oxyhydrochlorination of trichloroethane.

The contaminating chlorinated hydrocarbons present in the liquid feed composition can vary and are a function of the process used to prepare 1,2-dichloroethene, or the process used to prepare other chlorinated hydrocarbons from which a liquid composition comprising 1,2-dichloroethene is obtained. Non-limiting examples of such chlorinated hydrocarbons, e.g., $C_1$ and/or $C_2$ chlorinated hydrocarbons, include chloroform, methylene chloride, carbon tetrachloride, vinylidene chloride, vinyl chloride, trichloroethane, trichloroethylene, ethyl chloride, ethylene dichloride, perchloroethylene, pentachloroethane and mixtures of at least two of said chlorinated hydrocarbons. Materials other than chlorinated hydrocarbons, such as hydrogen chloride (HCl) and water can also be present in the liquid feed composition.

Organic free-radical initiators that can be used to isomerize the cis-isomer of 1,2-dichloroethene to the trans-isomer in the liquid phase can be chosen from a wide variety of organic free-radical initiators.

One contemplated class of organic free-radical initiators is organic peroxygen-containing compounds, which class can be subdivided into a number of subclasses, which include peroxides, hydroperoxides, ketone peroxides, aldehyde peroxides, diperoxyketals, diacyl peroxides, peroxycarboxylic acids, peroxyesters, peroxycarbonates, peroxydicarbonates and azo-nitrile organic initiators. Non-limiting examples of such organic free-radical initiators include the following:

Peroxides, exemplified by diethyl peroxide, di-tert-butyl peroxide [CAS 110-05-4], n-butyl 4,4-bis(tert-butylperoxy) valerate, 1,1-bis(tert-butylperoxy)-3,3,5-trimethylcyclohexane, bis-tert-butyl peroxides of diisopropylbenzene, dicumyl peroxide [CAS-80-43-3], 2,5-dimethyl-2,5-bis(tert-butylperoxy)hexane [CAS 78-63-7], and 2,5-dimethyl-2,5-bis(tert-butylperoxy)-3-hexyne [GAS 1068-27-5];

Hydroperoxides exemplified by methyl hydroperoxide, tert-butyl hydroperoxide [CAS 75-91-2], cumyl hydroperoxide [CAS 80-15-9], 2,5-dimethyl-2,5-dihydroperoxy-hexane [CAS 3025-88-5], p-menthanehydroperoxide [CAS 80-47-7], and diisopropylbenzene hydroperoxide [CAS 98-49-7];

Ketone peroxides, exemplified by methyl ethyl ketone peroxide, methyl isobutyl ketone peroxide, cyclohexanone peroxide, 2,4-pentanedione peroxide, the 1,2,4,5-tetraoxacyclohexanes, and the 1,2,4,5,7,8-hexaoxacyclononanes;

Aldehyde peroxides, exemplified by bis(10hydroxyheptyl) peroxide;

Diperoxyketals, exemplified by 2,2-bis(tert-butyl-peroxy) butane [CAS 2167-23-9], ethyl 3,3-bis(tert-butylperoxy)butyrate [CAS 55794-20-2], 1,1-bis(tert-butylperoxy)cyclohexane [3006-86-8], and 1,1-bis(tert-butylperoxy)-3,3,5-trimethyl-cyclohexane [CAS 6731-36-8];

Diacyl peroxides, exemplified by diacetyl peroxide [CAS 110-22-5] dibenzoyl peroxide [CAS 94-36-0], dicaprylyl peroxide, bis(4-chlorobenzoyl) peroxide, didecanoyl peroxide, bis(2,4-dichlorobenzoyl) peroxide [CAS 133-14-2], diisobutyryl peroxide [CAS 3437-84-1], diisononanoyl peroxide, dilauroyl peroxide [CAS 105-74-8], dipelargonyl peroxide, dipropionyl peroxide, and bis(3-carboxylpropionyl) peroxide;

Peroxycarboxylic acids, exemplified by peroxyacetic acid;

Peroxyesters, exemplified by tert-butyl peroxyacetate [CAS 107-71-1], methyl peroxyacetate, tert-butyl peroxybenzoate [CAS 614-45-9] tert-butyl peroxy(2-ethylhexanonate) [CAS 3006-82-4], tert-butyl peroxyisobutyrate, tert-butyl peroxypivalate, 2,5-dimethyl-2,5-bis(benzoylperoxy)hexane [CAS 618-77-1], tert-butyl peroxy(2-ethylbutyrate), 2,5-dimethyl-2,5-bis(2-ethylhexanoylperoxy)-hexane [CAS 13052-09-0], di-tert-butyl-diperoxyazelate [CAS16580-06-6], tert-amyl peroxy(2-ethylhexanoate) [CAS 686-31-7], di-tert-butyldiperoxyphthalate, O,O-tert-butyl hydrogen monoperoxymaleate, dimethyl peroxyoxalate, di-tert-butyl diperoxyoxalate, and tert-butyl peroxyneodecanoate [CAS 748-41-4];

Peroxycarbonates, exemplified by tert-butylperoxy isopropyl carbonate; and

Peroxydicarbonates, exemplified by diisopropyl peroxydicarbonate [CAS 105-64-6], di-sec-butyl peroxydicarbonate, di-n-propyl peroxydicarbonate [CAS 16066-38-9], di(2-ethylhexyl) peroxydicarbonate, dicyclohexyl peroxydicarbonate [CAS 1561-49-5], and dicetyl peroxydicarbonate [CAS 26322-14-5];

Another class of organic free-radical initiators that can be used in the method of the present invention comprises the organic azonitrile initiators, of which there are many. Examples of suitable azo-nitrile initiators include, but are not limited to, 2,2'-azobis(2-methylpropanenitrile) [CAS 78-67-1], which is often referred to by the abbreviation AIBN, 2,2'-azobis(2-methylbutanenitrile) [CAS 13472-08-7], 2,2'-azobis(2,4-dimethylpentanenitrile) [CAS 4419-11-8], 2,2'-azobis(4-methoxy-2,4-dimethylpentanenitrile) [CAS 15545-97-8], 1,1'-azobis(cyclohexanecarbonitrile) [CAS 2094-98-6], 4,4'-azobis(4-cyanopentanoic acid) [CAS 2638-94-0], 2,2'-azobis(2-methylpentanenitrile), 2,2'-azobis (2,3-dimethyl-butanenitrile), 2,2'-azobis(2-methylhexanenitrile), 2,2'-azobis(2,3-dimethylpentanenitrile), 2,2'-azobis(2,3,3-trimethylbutanenitrile), 2,2'-azobis(2,4,4-trimethylpentanenitrile), 2,2'-azobis(2-methyl-3-phenylpropanenitrile), 2,2'-azobis(2-cyclohexylpropanenitrile), 1,1'-azobis(cycloheptanecarbonitrile), 1,1'-azobis(cyclooctanecarbonitrile), 1,1'-azobis(cyclodecanecarbonitrile), 2-(tert-butylazo)-4-methoxy-2,4-dimethylpentanitrile [CAS 55912-17-9], 2-(tert-butylazo)-2,4-dimethylpentanenitrile [CAS 55912-18-0], 2-(tert-butylazo)-2-methylpropanenitrile [CAS 25149-46-6], 2-(tert-butylazo)-2-methylbutanenitrile [CAS 52235-20-8], 1-(tert-amylazo)cyclohexanecarbonitrile [CAS 55912-19-1], 1-(tert-butylazo) cyclohexanecarbonitrile [CAS 25149-47-7], and 2-[(1-chloro-1-phenylethyl) azo]-2-phenylpropanenitrile.

Another class of organic free-radical initiators that can be used in the method of the present invention is metallic organic free-radical initiators. Examples of such metallic organic free-radical initiators include, but are not limited to, diethyloxyaluminum tert-cumyl peroxide [CAS 34914-67-5], tri-tert-butyl perborate [CAS 22632-09-3], tert-butyl triethylgermanium peroxide [CAS 26452-74-4], dioxybis [triethylgermane] [CAS 58468-05-6], (tert-butyldioxy)triethylplumbane [CAS 18954-12-6], OO-tert-butyl dimethyl phosphorperoxoate [CAS 18963-64-9], tetrakis(tert-butyl) peroxysilicate [CAS 10196-46-0], dioxybis[trimethylsilane] [CAS 5796-98-5], (tert-butyldioxy)trimethylsilane [CAS 3965-63-7], dioxybis[triethylstannane] [CAS 4403-63-8], and (tert-butyldioxy)trimethylstannane [CAS 20121-56-6]. Other examples are given in Kirk-Othmer Encyclopedia of Chemical Technology, third edition, Volume 17, pages 2-22, 34, 49-50, 54-55, and 59 (1982), which is incorporated by reference herein.

The amount of free-radical initiator present in the liquid phase during the reaction can vary and is, in part, a function of the particular free-radical initiator chosen. In general, the free-radical initiator is present in amounts sufficient to initiate and promote the isomerization reaction, e.g., an initiating amount. The minimum amount of free-radical initiator is a function of the preceding requirement, while the maximum amount is not limited by any particular theory, but by practical and economic factors. Since initiator deactivation is likely to occur to at least some degree as the isomerization reaction progresses and since it is difficult to ascertain how much active free-radical initiator is present at any given instant in the reactive distillation zone, the relative proportions of free-radical initiator and 1,2-dichloroethene (both stereoisomers) are best expressed in terms of the amount of free-radical initiator charged to the isomerization reaction zone based on the amount of 1,2-dichloroethene in the feed to the isomerization reaction zone, although it should be recognized that the amount of active free-radical initiator present in the reaction zone is probably less at most times. If free-radical initiator deactivation is significant during the isomerization reaction, the addition of free-radical initiator to the isomerization reaction zone can be made intermittently or continuously to remedy such deactivation. The manner in which the free-radical initiator is introduced into the reaction zone will, of course, depend on whether the reaction is conducted batch wise, semi-batch wise, continuously or semi-continuously.

The amount of free-radical initiator charged to the isomerization reaction zone can vary widely. In one non-limiting embodiment, it typically can vary from 5 to 5000 parts of free-radical initiator per million parts (weight basis) of 1,2-dichloroethene (both isomers) (ppm) in the feed charged to the isomerization reaction zone. Often, the weight ratio of free-radical initiator to 1,2-dichloroethene ranges from 5 to 2000 ppm. Frequently, the weight ratio is in the range of from 20 to 1500 ppm, e.g., from 25 to 1000 ppm, more particularly from 25 to 500, e.g., from 100 to 250 ppm. The weight ratio of free-radical initiator to 1,2-dichloroethene (both isomers) can vary between any combination of any of the foregoing lower and higher stated values, inclusive of the recited values.

In accordance with one embodiment of the process of the present invention, a liquid chlorinated hydrocarbon feed containing the cis- and trans-stereoisomers of 1,2-dichloroethene and substantial contaminating amounts of other chlorinated hydrocarbons, e.g., chlorinated hydrocarbons containing 1 and 2 carbon atoms, is charged to a first separation zone, e.g., a first distillation zone comprising at least one distillation column, wherein a first fraction, e.g., a light fraction, comprising the stereoisomers of 1,2-dichloroethene and chlorinated hydrocarbons more volatile than said stereoisomers are separated from the heavier fraction of the liquid hydrocarbon feed stream, the lighter fraction being removed from the upper part of the separation zone, e.g., as an overhead stream from the first distillation column. If required for efficient fractional separation of the components in the feed, a portion of the light fraction can be condensed and returned to a section near the top of the first distillation column as a reflux stream.

The light fraction from the first distillation zone, e.g., the first distillation column, is typically condensed and at least a portion of the resulting distillate is forwarded to a second separation zone, e.g., a second distillation zone comprising at least one distillation column, wherein chlorinated hydrocarbons more volatile than the stereoisomers of 1,2-dichloroethene are separated from the stereoisomers of 1,2-dichloroethene and removed as a second fraction, e.g., as an overhead stream, from the upper part of the second separation zone, e.g., a second distillation column.

Liquid effluent, e.g., a third liquid fraction, comprising the stereoisomers of 1,2-dichloroethene is recovered from the second separation zone, e.g., from or near the bottom of the second distillation zone, such as a distillation column, and at least a portion of such effluent is forwarded to a reaction zone, e.g., a further distillation column. The liquid effluent recovered from the second separation zone comprises principally the stereoisomers of 1,2-dichloroethene, e.g., at least 85 weight percent, often at least 90 weight percent, of the isomers. The cis-stereoisomer of 1,2-dichloroethene is isomerized to the trans-stereoisomer in the reaction zone, e.g., a reaction distillation zone that can comprise a distillation column, in the liquid phase in the presence of an effective amount, e.g., an initiating amount of at least one free-radical initiator. The trans-1,2-dichloroethene isomer is recovered as a substantially pure product, e.g., the product comprises at least 90 weight percent, often at least 95 weight percent, and frequently at least 99 weight percent of trans-1,2-dichloroethene, from the reaction distillation zone, e.g., as overhead from the reaction distillation zone.

In accordance with a further embodiment of the process of the present invention, a liquid chlorinated hydrocarbon feed containing the cis- and trans-stereoisomers of 1,2-dichloroethene and substantial contaminating amounts of other chlorinated hydrocarbons, e.g., chlorinated hydrocarbons containing 1 and 2 carbon atoms, is charged to a first separation zone, e.g., a first distillation zone comprising at least one distillation column, wherein a light fraction comprising chlorinated hydrocarbons more volatile than said stereoisomers are separated from the stereoisomers and chlorinated hydrocarbons less volatile than the cis- and trans-stereoisomers, the lighter fraction being removed from the upper part of the first separation zone, e.g., as an overhead stream from the first distillation column. If required for efficient fractional separation of the components in the feed, a portion of the light fraction removed as overhead from the first separation zone can be condensed and returned to a section near the top of the first distillation column as a reflux stream.

The fraction comprising the cis- and trans-isomers and chlorinated hydrocarbons less volatile (having a higher boiling temperature) than the stereoisomers that is recovered from the first separation zone, e.g., from the first distillation column, is forwarded to a second separation zone, e.g., a second distillation zone comprising at least one distillation column, wherein chlorinated hydrocarbons less volatile than the stereoisomers of 1,2-dichloroethene are separated from the stereoisomers of 1,2-dichloroethene, which are removed from the upper part of the second separation zone, e.g., as an overhead stream from the second distillation column. In this embodiment, it is likely that trace quantities of hydrogen chloride will be present in the overhead stream from the second separation zone. Accordingly, it is contemplated that this overhead stream can be treated with an alkaline reagent, e.g., sodium hydroxide, to neutralize the hydrogen chloride, thereby avoiding any deleterious affects the hydrogen chloride can have on the initiator and/or isomerization reaction that subsequently follows. The fraction recovered from the second separation zone, e.g., from the second distillation column, comprises principally the trans- and cis-isomers of 1,2-dichloroethene, e.g., at least 85 weight percent, often at least 90 weight percent, of the isomers.

At least a portion of the effluent fraction comprising the stereoisomers of 1,2-dichloroethene recovered from the second separation zone is forwarded to a reaction zone, e.g., a reaction distillation zone comprising at least one distillation column. The cis-stereoisomer of 1,2-dichloroethene is isomerized to the trans-stereoisomer in the reaction zone in the liquid phase in the presence of an effective amount, e.g., an initiating amount, of at least one free-radical initiator. The trans-1,2-dichloroethene isomer is recovered as a substantially pure product, e.g., the product comprises at least 90 weight percent, often at least 95 weight percent, and frequently at least 99 weight percent of trans-1,2-dichloroethene, from the reaction distillation zone, e.g., as overhead from the reaction distillation zone.

Referring now to the accompanying FIGURE wherein one embodiment of the present process is illustrated, there are shown three distillation columns, each having an associated condenser and reboiler. While three columns are shown, it is possible to use one or more of the described columns for one or more of the described distillations, e.g., using a batch distillation procedure rather than the continuous distillation method shown in the FIGURE. In such a case, the product from a particular distillation that is to be further distilled is first collected, and then used as feed to the distillation column.

A liquid feed composition 11 comprising stereoisomers of 1,2-dichloroethene and contaminating amounts of other more volatile and less volatile chlorinated hydrocarbons is charged to the first distillation column 10. As shown, the liquid feed composition is charged to the first distillation column near the midpoint of the column. The precise point at which the liquid feed composition is introduced into the first column is not critical, however in one embodiment, the feed composition is typically introduced at a point somewhere within the midsection of the column. In column 10, the stereoisomers of 1,2-dichloroethene and materials more volatile than the stereoisomers are separated from materials that are less volatile (and heavier) than the stereoisomers of 1,2-dichloroethene, e.g., the heavy fraction, in the liquid feed composition.

The stereoisomers of 1,2-dichloroethene and the materials more volatile than these stereoisomers are removed as vaporous effluent from near the top of column 10 by line 12 and forwarded to condenser 15, e.g., a shell and tube condenser. The condensate (distillate) from condenser 15 is forwarded by line 16 to T 17 where it is split into two portions. One portion is returned to column 10 as reflux by line 19, while the remaining portion is forwarded by line 18 to the second distillation column 20. The portion of distillate returned to column 10, e.g., the reflux ratio, is controlled by valves 2 and 3 in lines 19 and 18 respectively. If desired, a distillate storage tank (not shown) can be positioned to receive distillate from condenser 15, and distillate from the distillate storage tank forwarded to columns 10 (as reflux) and 20 (as feed). Non-condensable materials removed as overhead from column 10 can be vented through a vent in line 16 (not shown) or from the distillate storage tank and forwarded for treatment.

The heavy fraction of the liquid feed composition 11, e.g., the materials less volatile than the 1,2-dichloroethene isomers, are removed from column 10 through line 14. The heavy fraction can be recycled to the source of the liquid feed composition or treated as a waste stream depending on its composition and economic value. A portion of the heavy fraction removed from column 10 can be forwarded by line 13 to reboiler 8, into which steam is introduced by means of line 45. Reboiler 8 can be a typical shell and tube heat exchanger. Condensed steam is removed from reboiler 8 by means of line 51. Reheated bottoms are returned to column 10 through line 9.

The construction of column 10, e.g., material of construction, size and number of distillation plates, will be a function of the components and their quantity in the liquid feed composition. One skilled in the art can readily calculate the requirements of column 10 in order to make the required separation between the lighter fraction comprising the stereoisomers of 1,2-dichloroethene and materials more volatile than such stereoisomers, and the less volatile materials (heavy fraction) in the liquid feed composition. The operating conditions for column 10 will also vary and are also a function of the components and their quantity in the liquid feed composition. Typically, column 10 will operate at temperatures in the range of 225 to 245° F. (107 to 118° C.) within or near the bottom section of the column and in the range of 165 to 205° F. (74 to 96° C.) within or near the top section of the column. Generally, the pressure at the top of column 10 will range from 5 to 15 psig.

Liquid distillate from condenser 15 is forwarded by line 18 as the feed stream to column 20. As shown, the feed stream is charged to the second distillation column 20 at a point near the midpoint of the column. The precise point at which the feed stream is introduced into column 20 is not critical, however the feed steam is typically introduced at a point somewhere within the midsection of the column. In column 20, the stereoisomers of 1,2-dichloroethene and materials more volatile than the stereoisomers are separated from one another, with the more volatile materials being removed as overhead from column 20 and the stereoisomers being removed at or near the bottom section of column 20 by means of line 24. The more volatile materials are forwarded by line 22 to condenser 25 where they are condensed. Condensate from condenser 25 is forwarded by line 23 to T 26 where it is split into two portions. One portion can be returned to column 20 by line 28 as reflux, while the remaining portion is forwarded by line 27 for further processing, e.g., recycle, recovery or to a waste treatment facility. The portion of distillate returned to column 20, e.g., the reflux ratio, is controlled by valves 4 and 5.

A portion of the bottoms fraction from column 20 is forwarded to reboiler 21 by line 29, into which steam is introduced by means of line 46. Reboiler 21 can be a typical shell and tube heat exchanger. Condensed steam is removed from reboiler 21 by means of line 52. Reheated bottoms are returned to column 20 through line 48.

The construction of column 20, e.g., material of construction, size and number of distillation plates, will be a function of the components and their quantity in feed stream 18. One skilled in the art can readily calculate the requirements of column 20 in order to make the required separation between the stereoisomers of 1,2-dichloroethene and materials more volatile than the stereoisomers. The operating conditions for column 20 can also vary and are also a function of the components and their quantity in feed stream 18. Typically, column 20 operates at temperatures in the range of 150 to 175° F. (66 to 79° C.) within or near the bottom section of the column and in the range of 120 to 150° F. (49 to 66° C.) within or near the top section of the column. Generally, the pressure at the top of column 20 will range from 4 to 15 psig.

Liquid effluent withdrawn from near or at the bottom of column 20 is forwarded by line 24 as the feed to reaction distillation column 30. Feed stream 24 comprises predominantly the stereoisomers of 1,2-dichloroethene, although other minor amounts of other chlorinated hydrocarbons can be present in the feed stream. Free-radical initiator from tank 40 is charged to column 30 by line 44. The amount of free-radical initiator introduced into column 30 is controlled by control means, e.g., valve, 42. Typically, the free-radical initiator is combined in tank 40 with trans-1,2-dichloroethene and the resultant mixture, e.g., solution, slurry, etc., is forwarded to column 30. When combined with the feed stream 24, the amount of free-radical initiator in column 30 will be in the amounts described previously, e.g., initiating amounts.

The desired trans-1,2-dichloroethene is removed from the top of column 30 by line 32 and forwarded to condenser 35, e.g., a typical shell and tube heat exchanger. Condensate (distillate) from condenser 35 is forwarded by line 33 to T 36 where it can be split into two portions if column 30 is operated under reflux conditions. The portion returned by column 30 is forwarded by line 38 to column 30, while the portion taken as product is forwarded by line 37 to product storage or further treatment, if required. Typically, the trans-1,2-dichloroethene product is substantially pure, e.g., the product comprises at least 90 weight percent, often at least 95 weight percent and frequently at least 99 weight percent of trans-1,2-dichloroethene, and hence does not require further distillation to improve its purity. The portion of condensate returned to column 30 as reflux is controlled by valves 6 and 7. An effluent comprising cis-1,2-dichloroethene is removed from column 30 at or near the bottom of column 30 through line 34.

A portion of the bottoms fraction removed from column 30 is forwarded to reboiler 31 by means of line 39. Steam is introduced into reboiler 31, e.g., a typical shell and tube heat exchanger, by means of line 47. Condensed steam is removed from reboiler 31 by means of line 53. Reheated bottoms from column 30 are returned to the column through line 49.

The construction of column 30, e.g., material of construction, size and number of distillation plates can be readily determined by one skilled in the art order to make the required separation between the stereoisomers of 1,2-dichloroethene. The temperature of the isomerization reaction can vary; however, temperatures will typically be in the range of from 185 to 235° F. (85 to 113° C.) near the bottom section of the column and from 140 to 175° F. (60 to 79° C.) near the top section of the column.

Generally, the pressure at the top of column 30 will range from 5 to 15 psig. The reaction temperature can be varied by increasing or decreasing the pressure on column 30.

The invention is further described in conjunction with the following example, which is to be considered as illustrative rather than limiting, and in which all parts are by weight and all percentages are percentages by weight unless otherwise specified.

EXAMPLE

A liquid feed composition comprising approximately 3.4 weight percent of vinylidene chloride, 38.4 weight percent of trans-1,2-dichloroethene, 28.5 weight percent of cis-1,2-dichloroethene, 2.2 weight percent of chloroform, 2.0 weight percent of carbon tetrachloride, and 17.1 weight percent of trichloroethylene was charged to a first distillation column, e.g., column 10. Small amounts of hydrogen chloride, methylene chloride, water, ethyl chloride, vinyl chloride, ethylene dichloride, 1,1,2-trichloroethane, perchloroethylene and pentachloroethane, which together totaled 8.4 weight %, were also present in the feed composition. The composition of the overhead from this first distillation was approximately 4.6 weight percent vinylidene chloride, 49.2 weight percent of trans-1,2-dichloroethene, 46.2 weight percent of cis-1,2-dichloroethene, and trace quantities of lighter boiling hydrocarbons. The temperature and pressure at the top of the first column were approximately 201° F. (94° C.) and 10 psig respectively. The composition of the bottom fraction from this first distillation was approximately 0.4 weight percent of trans-1,2-dichloroethene, 11.6 weight percent of cis-1,2-dichloroethene, 3.9 weight percent of chloroform, 37.2 weight percent of carbon tetrachloride, 0.9 weight percent of ethylene dichloride and 45.7 weight percent of trichloroethylene. The temperature and pressure at the bottom of the first column were approximately 236° F. (113° C.) and 18.6 psig respectively. The first column was operated at a reflux ratio of 18 (reflux to column feed basis).

A portion of the overhead withdrawn from the first column was charged to a second distillation column. The composition of the bottom fraction from the second column was approximately 71.7 weight percent of trans-1,2-dichloroethene and 27.4 weight percent of cis-1,2-dichloroethene, the balance being composed of other chlorinated hydrocarbons. The composition of the overhead from the second column was approximately 48.1 weight percent of trans-1,2-dichloroethene, the balance being composed of other chlorinated hydrocarbons. The second column was operated at a reflux ratio of 3.4 (reflux to column feed basis). The temperature and pressure at the top of the second column was approximately 144° F. (62° C.) and 15 psig respectively. The temperature and pressure at the bottom of the second column was approximately 172° F. (78° C.) and 18 psig respectively.

The bottom fraction from the second distillation column was introduced into a reactive distillation column. In this column cis-1,2-dichloroethene was isomerized to the trans-isomer in the liquid phase and in the presence of approximately 240 ppm of azobisisobutyronitrile [AIBN]. This column was operated at a reflux ratio of 14 (reflux to column feed basis). The temperature and pressure at the bottom of the reactive distillation column was approximately 204° F. (96° C.) and 17 psig respectively. The composition of the bottoms fraction removed from the reactive distillation column was approximately 12.0 weight percent trans-1,2-dichloroethene, 18.7 weight percent of cis-1,2-dichloroethene, 8.5 weight percent of chloroform, and 46.4 weight percent of carbon tetrachloride. The composition of the overhead from the reactive distillation column was approximately 99.9 weight percent trans-1,2-dichloroethene and 0.1 weight percent of cis-1,2-dichloroethene. The temperature and pressure at the top of the third column was approximately 150° F. (66° C.) and 10 psig respectively.

The foregoing example demonstrates that the process of the present invention can provide trans-1,2-dichloroethene in concentrations of greater than 99% purity. A material balance for the foregoing example established that the method described can recover more than 95% of the 1,2-dichloroethene from a feed composition containing contaminating amounts of higher and lower boiling chlorinated hydrocarbons.

Although, the present invention has been described with reference to specific details of certain embodiments thereof, it is not intended that such details should be regarded as limitations upon the scope of the invention except insofar as they are included in the accompanying claims.

What is claimed is:

1. A method for recovering trans-1,2-dichloroethene from a liquid composition comprising the stereoisomers trans-1,2-dichloroethene and cis-1,2-dichloroethene, and contaminating amounts of other chlorinated hydrocarbons, comprising:
    (a) distilling said liquid composition in a first distillation zone;
    (b) removing first distillate comprising said stereoisomers trans-1,2-dichloroethene and cis-1,2-dichloroethene, and chlorinated hydrocarbons having a lower boiling temperature than said stereoisomers from said first distillation zone;
    (c) distilling at least a portion of the first distillate in a second distillation zone, and removing a liquid stream comprising said stereoisomers from the second distillation zone;
    (d) introducing at least a portion of the liquid stream comprising said stereoisomers removed from the second distillation zone into a reactive distillation zone containing organic free-radical initiator;
    (e) isomerizing cis-1,2-dichloroethene to trans-1,2-dichloroethene in said reactive distillation zone; and
    (f) recovering substantially pure trans-1,2-dichloroethene product from said reactive distillation zone.

2. The method of claim 1 wherein the contaminating amount of other chlorinated hydrocarbons comprise at least 20 weight percent of the liquid composition.

3. The method of claim 1 wherein the contaminating amount of other chlorinated hydrocarbons comprise from 20 to 80 weight percent of the liquid composition.

4. The method of claim 1 wherein the other chlorinated hydrocarbons comprise $C_1$-$C_2$ chlorinated hydrocarbons.

5. The method of claim 4 wherein the other chlorinated hydrocarbons comprise from 30 to 70 weight percent of the liquid composition.

6. The method of claim 4 wherein the chlorinated hydrocarbons are chosen from chloroform, methylene chloride, carbon tetrachloride, vinylidene chloride, vinyl chloride, trichloroethane, trichloroethylene, ethyl chloride, ethylene dichloride, perchloroethylene, pentachloroethane and mixtures of at least two of said chlorinated hydrocarbons.

7. The method of claim 1 wherein the free-radical initiator is an organic azonitrile initiator.

8. The method of claim 1 wherein the free-radical initiator is present in the reactive distillation zone in amounts of from 5 to 5000 ppm.

9. The method of claim 1 wherein the free-radical initiator is present in the reactive distillation zone in amounts of from 100 to 2000 ppm.

10. The method of claim 7 wherein the initiator is azobisisobutyronitrile.

11. The method of claim 10 wherein the azobisisobutyronitrile is present in amounts of from 25 to 1000 ppm.

12. The method of claim 10 wherein the temperature at which the cis-isomer is isomerized to the trans-isomer is from 190° F. to 235° F.

13. A method for recovering trans-1,2-dichloroethene from a liquid composition comprising the stereoisomers trans-1,2-dichloroethene and cis-1,2-dichloroethene, and from 35 to 65 weight percent of other chlorinated hydrocarbons, comprising:
    (a) distilling said liquid composition in a first distillation zone;
    (b) removing first distillate comprising said stereoisomers trans-1,2-dichloroethene and cis-1,2-dichloroethene, and chlorinated hydrocarbons having a lower boiling temperature than said stereoisomers from said first distillation zone;
    (c) distilling at least a portion of the first distillate in a second distillation zone, and removing a liquid stream comprising said stereoisomers from the second distillation zone;
    (d) introducing at least a portion of the liquid stream comprising said stereoisomers removed from the second distillation zone into a reactive distillation zone containing organic free-radical initiator;
    (e) isomerizing cis-1,2-dichloroethene to trans-1,2-dichloroethene in the liquid phase in said reactive distillation zone; and
    (f) recovering substantially pure trans-1,2-dichloroethene product from said reactive distillation zone.

14. The method of claim 13 wherein the other chlorinated hydrocarbons comprise $C_1$-$C_2$ chlorinated hydrocarbons.

15. The method of claim 14 wherein the chlorinated hydrocarbons are chosen from chloroform, methylene chloride, carbon tetrachloride, vinylidene chloride, vinyl chloride, trichloroethane, trichloroethylene, ethyl chloride, ethylene dichloride, perchloroethylene, pentachloroethane and mixtures of at least two of said chlorinated hydrocarbons.

16. The method of claim 13 wherein the free-radical initiator is an organic azonitrile initiator that is present in the reactive distillation zone in amounts of from 5 to 2000 ppm.

17. The method of claim 16 wherein the free-radical initiator is azobisisobutyronitrile, which is present in amounts of from 25 to 1000 ppm.

18. The method of claim 17 wherein the temperature at which the cis-isomer is isomerized to the trans-isomer is from 190° F. to 235° F.

19. A method for recovering trans-1,2-dichloroethene from a liquid composition comprising the cis- and trans-stereoisomers of 1,2-dichloroethene and contaminating amounts of other chlorinated hydrocarbons, comprising:
    (a) separating the cis- and trans- stereoisomers of 1,2-dichloroethene and chlorinated hydrocarbons more volatile than said stereoisomers as a first fraction from said liquid composition in a first separation zone;
    (b) introducing at least a portion of the first fraction removed from the first separation zone into a second separation zone, and removing as a second fraction from the second separation zone chlorinated hydrocarbons more volatile than said stereoisomers of 1,2-dichloroethene;
    (c) removing a third fraction comprising the cis- and trans- stereoisomers of 1,2-dichloroethene from the second separation zone;
    (d) introducing at least a portion of the third fraction comprising the cis- and trans- stereoisomers of 1,2-dichloroethene removed from the second separation zone into a reaction zone;
    (e) isomerizing cis-1,2-dichloroethene to trans-1,2-dichloroethene within said reaction zone, said isomerization being conducted in the liquid phase and in the presence of an organic free-radical initiator; and
    (f) recovering substantially pure trans-1,2-dichloroethene product from said reaction zone.

20. The method of claim 19 wherein the other chlorinated hydrocarbons comprise $C_1$-$C_2$ chlorinated hydrocarbons and are present in the liquid composition in amounts of from 20 to 80 weight percent.

21. The method of claim 20 wherein the other chlorinated hydrocarbons are chosen from chloroform, methylene chloride, methyl chloroform, carbon tetrachloride, vinylidene chloride, vinyl chloride, trichloroethane, trichloroethylene, ethyl chloride, ethylene dichloride, perchloroethylene, pentachloroethane and mixtures of at least two of said chlorinated hydrocarbons.

22. The method of claim 21 wherein the free-radical initiator is an organic azonitrile initiator, which is present in the reactive distillation zone in amounts of from 5 to 2000 ppm.

23. The method of claim 22 wherein the azonitrile initiator is azobisisobutyronitrile, which is present in amounts of from 25 to 1000 ppm.

24. A method for recovering trans-1,2-dichloroethene from a liquid composition comprising the stereoisomers trans-1,2-dichloroethene and cis-1,2-dichloroethene, and contaminating amounts of other chlorinated hydrocarbons, comprising:
    (a) distilling said liquid composition in a first distillation zone;
    (b) separating in said first distillation zone chlorinated hydrocarbons more volatile than the stereoisomers trans-1,2-dichloroethene and cis-1,2-dichloroethene from the liquid composition, thereby to produce a second liquid composition comprising said stereoisomers;
    (c) distilling at least a portion of said second liquid composition in a second distillation zone, and removing an overhead stream comprising principally trans-1,2-dichloroethene and cis-1,2-dichloroethene from said second distillation zone;
    (d) introducing at least a portion of the overhead stream from the second distillation zone into a reactive distillation zone containing organic free-radical initiator;
    (e) isomerizing cis-1,2-dichloroethene to trans-1,2-dichloroethene in said reactive distillation zone; and
    (f) recovering substantially pure trans-1,2-dichloroethene product from said reactive distillation zone.

25. The method of claim 24 wherein the contaminating amount of other chlorinated hydrocarbons comprise from 20 to 80 weight percent of the liquid composition.

26. The method of claim 25 wherein the other chlorinated hydrocarbons comprise $C_1$-$C_2$ chlorinated hydrocarbons.

27. The method of claim 26 wherein the chlorinated hydrocarbons are chosen from chloroform, methylene chloride, carbon tetrachloride, vinylidene chloride, vinyl chloride, trichioroethane, trichloroethylene, ethyl chloride, ethylene dichloride, perchloroethylene, pentachloroethane and mixtures of at least two of said chlorinated hydrocarbons.

28. The method of claim 24 wherein the free-radical initiator is an organic azonitrile initiator.

29. The method of claim 24 wherein the free-radical initiator is present in the reaction distillation zone in amounts of from 100 to 2000 ppm.

30. The method of claim 28 wherein the free-radical initiator is azobisisobutyronitrile.

31. The method of claim 30 wherein the azobisisobutyronitrile is present in the reactive distillation zone in amounts of from 25 to 1000 ppm.

32. The method of claim 30 wherein the temperature at which the cis-isomer is isomerized to the trans-isomer is from 190° F. to 235° F.

33. A method for recovering trans-1,2-dichloroethene from a liquid composition comprising the stereoisomers trans-1,2-dichloroethene and cis-1,2-dichloroethene, and contaminating amounts of other chlorinated hydrocarbons, comprising:
(a) fractionally distilling said liquid composition in a first distillation zone;
(b) removing first distillate comprising said stereoisomers trans-1,2-dichloroethene and cis-1,2-dichloroethene, and chlorinated hydrocarbons having a lower boiling temperature than said stereoisomers from said first distillation zone;
(c) fractionally distilling at least a portion of the first distillate in a second distillation zone, and removing a liquid fraction comprising principally said stereoisomers from the second distillation zone;
(d) introducing at least a portion of the liquid fraction comprising said stereoisomers removed from the second distillation zone into a reactive distillation zone containing organic free-radical initiator;
(e) isomerizing cis-1,2-dichloroethene to trans-1,2-dichloroethene in the liquid phase in said reactive distillation zone; and
(f) recovering substantially pure trans-1,2-dichloroethene product from said reactive distillation zone.

34. The method of claim 33 wherein the contaminating amount of other chlorinated hydrocarbons comprise at least 20 weight percent of the liquid composition and further comprise $C_1$-$C_2$ chlorinated hydrocarbons chosen from chloroform, methylene chloride, carbon tetrachloride, vinylidene chloride, vinyl chloride, trichioroethane, trichloroethylene, ethyl chloride, ethylene dichloride, perchloroethylene, pentachloroethane and mixtures of at least two of said chlorinated hydrocarbons.

35. The method of claim 34 wherein the organic free-radical initiator is an organic azonitrile initiator that is present in the reactive distillation zone in amounts of from 100 to 2000 ppm.

36. The method of claim 35 wherein the organic azonitrile initiator is azobisisobutyronitrile.

37. A method for recovering trans-1,2-dichloroethene from a liquid composition comprising the stereoisomers trans-1,2-dichloroethene and cis-1,2-dichloroethene, and contaminating amounts of other chlorinated hydrocarbons, comprising:
(a) distilling said liquid composition in a first distillation zone;
(b) recovering from said first distillation zone a composition comprising said stereoisomers trans-1,2-dichloroethene and cis-1,2-dichloroethene as either:
(1) an overhead stream comprising said stereoisomers and chlorinated hydrocarbons having a lower boiling temperature than said stereoisomers, or
(2) a liquid stream comprising said stereoisomers and chlorinated hydrocarbons having a higher boiling temperature than said stereoisomers;
(c) distilling at least a portion of said composition recovered from the first distillation zone in a second distillation zone;
(d) recovering from said second distillation zone a composition comprising principally trans-1,2-dichloroethene and cis-1,2-dichloroethene, and introducing at least a portion of said recovered composition into a reactive distillation zone containing organic free-radical initiator;
(e) isomerizing cis-1,2-dichloroethene to trans-1,2-dichloroethene in said reactive distillation zone; and
(f) recovering substantially pure trans-1,2-dichloroethene product from said reactive distillation zone.

38. The method of claim 37 wherein the contaminating amount of other chlorinated hydrocarbons comprise at least 20 weight percent of the liquid composition and further comprise $C_1$-$C_2$ chlorinated hydrocarbons chosen from chloroform, methylene chloride, carbon tetrachloride, vinylidene chloride, vinyl chloride, trichioroethane, trichloroethylene, ethyl chloride, ethylene dichloride, perchloroethylene, pentachloroethane and mixtures of at least two of said chlorinated hydrocarbons.

39. The method of claim 38 wherein the organic free-radical initiator is an organic azonitrile initiator that is present in the reactive distillation zone in amounts of from 100 to 2000 ppm.

40. The method of claim 39 wherein the organic azonitrile initiator is azobisisobutyronitrile.

41. The method of claim 40 wherein the azobisisobutyronitrile is present in amounts of from 25 to 1000 ppm, and the temperature at which the cis-isomer is isomerized to the trans-isomer is from 190° F. to 235° F.

* * * * *